United States Patent [19]

Periasamy

[11] Patent Number: 4,501,920

[45] Date of Patent: Feb. 26, 1985

[54] PREPARATION OF TRIMETHOXYBENZOATE SALTS AND TRIMETHOXYBENZOIC ACID

[75] Inventor: Muthunadar P. Periasamy, Creve Coeur, Mo.

[73] Assignee: Mallinckrodt, Inc., St. Louis, Mo.

[21] Appl. No.: 426,449

[22] Filed: Sep. 29, 1982

[51] Int. Cl.³ .................... C07C 65/00; C07C 69/76
[52] U.S. Cl. ....................................... 562/473; 560/64
[58] Field of Search .......................... 560/64; 562/473

[56] References Cited

PUBLICATIONS

Kutani, N. Chem. Pharm. Bull., vol. 8, pp. 72–76, 1960.

Britton et al., J. Chem. Soc., 1966, pp. 783–790.

*Primary Examiner*—Paul J. Killos
*Attorney, Agent, or Firm*—R. G. Jackson; L. N. Goodwin; R. J. Klostermann

[57] ABSTRACT

A salt of 3,4,5-trimethoxybenzoic acid is prepared by initially reacting hydrolyzable tannin with a methylation agent in an alkaline medium under methylation conditions to form methylated tannin and thereafter hydrolyzing the methylated tannin by reaction thereof with a hydrolysis agent under alkaline hydrolysis conditions. The resulting salt can be neutralized to form 3,4,5-trimethoxybenzoic acid, which can readily be recovered.

20 Claims, No Drawings

PREPARATION OF TRIMETHOXYBENZOATE SALTS AND TRIMETHOXYBENZOIC ACID

BACKGROUND OF THE INVENTION

This invention relates to a process for preparing 3,4,5-trimethoxybenzoate salts from hydrolyzable tannin and to a process for preparing 3,4,5-trimethoxybenzoic acid via preparation of such salts.

3,4,5-Trimethoxybenzoic acid (hereinafter sometime referred to as "TMB acid") is useful for preparing pharmaceutical compositions, e.g., trimethoprim. Heretofore, TMB acid has been prepared by a multiplicity of steps including (1) hydrolyzing tannin or a tannin-containing material to form gallic acid; (2) isolating the gallic acid; (3) methylating the isolated gallic acid to form a mixture of TMB acid and its methyl ester; (4) saponifying the acid-ester mixture; (5) acidifying the saponified mixture to liberate TMB acid from its salt; and (6) recovering the TMB-acid. Steps (1) and (2) involving tannin hydrolysis and gallic acid isolation are described in Krueger et al., U.S. Pat. No. 2,723,992. Japanese Patent 56-123938 indicates that methylation of gallic acid and one or more of the remaining steps are described in *Org. Syn. Coll.*, Vol. I, 537, *Corriere Favm.*, 22, 196 (1967). The foregoing highly multiple step process suffers a number of drawbacks, including need for isolation of gallic acid, high cost, and long reaction time where the tannin is hydrolyzed to gallic acid under acid hydrolysis conditions and decomposition of gallic acid to pyrogallic acid where such tannin hydrolysis is effected under alkaline conditions. Accordingly, there is a substantial need in the art for improved processes for preparing TMB acid and related TMB compounds.

It has now been found that TMB acid and salts thereof can be formed by an improved process which obviates the need for hydrolyzing tannin to gallic acid and isolating intermediates.

DESCRIPTION OF THE INVENTION

Generally stated, the present invention provides a process for preparing a salt of 3,4,5-trimethoxybenzoic acid, which comprises:
(a) reacting hydrolyzable tannin with a methylation agent in an alkaline medium under methylation conditions to form methylated tannin, and
(b) hydrolyzing the methylated tannin by reaction thereof with a hydrolysis agent under alkaline hydrolysis conditions to form a 3,4,5-trimethoxybenzoate salt of the hydrolysis agent.

This invention also provides a process for preparing 3,4,5-trimethoxybenzoic acid (TMB acid) which comprises:
(a) reacting hydrolyzable tannin with a methylation agent in an alkaline medium under methylation conditions to form methylated tannin,
(b) hydrolyzing the methylated tannin by reaction thereof with a hydrolysis agent under alkaline hydrolysis conditions to form a 3,4,5-trimethoxybenzoate salt of the hydrolysis agent, and
(c) neutralizing the trimethoxybenzoate salt to form 3,4,5-trimethoxybenzoic acid.

DETAILED DESCRIPTION OF THE INVENTION

In the first step of the process, hydrolyzable tannin is reacted with a methylation agent in an alkaline medium under methylation conditions to form methylated tannin. The tannin or tannic acid employed can be any hydrolyzable tannin such as that obtained by extraction thereof from such tannin-containing materials as tara pods, Chinese nut galls, Aleppo galls, sumac leaves, etc. Taratannin (i.e., tannin obtained by extraction from tara pods) is preferred. Methods for extracting tannin from tannin-containing materials are well known in the art.

Any suitable methylation agent can be used. Suitable methylation agents include, for example, dimethyl sulfate, methyl p-toluene sulfonate, methyl iodide, diazomethane etc. Dimethyl sulfate is preferred.

Any suitable alkaline medium can be employed for the methylation reaction. The alkaline medium includes a liquid solvent or dispersant such as water, ethyl acetate, methyl isobutyl ketone, acetone, etc. and an alkaline agent such as sodium hydroxide, potassium hydroxide, calcium hydroxide, ammonium hydroxide, organic amines (e.g., triethylamine), etc. Aqueous sodium hydroxide is preferred for the alkaline medium.

The methylation reaction is effected, for example, by initially forming a reaction mixture of the tannin, methylation agent (e.g., dimethyl sulfate), alkaline agent or base (e.g., sodium hydroxide), and the liquid solvent or dispersant (e.g., water). The methylation reaction may then be effected under any suitable methylation conditions, including for example heating with agitation at a temperature of about 15° to about 80° C. for a period of about 2 to about 8 hours.

The methylation agent is preferably employed in an amount at least equal to the stoichiometric amount required for conversion of all the hydroxyl groups of the tannin to methoxy groups. More preferably, a stoichiometric excess of the methylation agent is employed. The alkaline agent must be included in a sufficient amount such that the reaction mixture is above 7 pH, preferably at least 8 pH and more preferably at least 10 pH.

Where the tannin is taratannin and the methylation agent is dimethyl sulfate, the amount of dimethyl sulfate may be from 2.5 to about 5.0 parts by weight per one part by weight of taratannin. Corresponding molar ratios of other methylation agents can be employed for methylation of taratannin or other tannins. The amount of sodium hydroxide may be from about 1.25 to about 2.25 parts by weight of NaOH per one part by weight of taratannin. Corresponding molar ratios of other alkaline agents can be employed for taratannin or other tannins. As a general preference the base is employed as a 50% aqueous solution. Thus, for example, from about 2.5 to about 4.5 parts by weight of 50% aqueous sodium hydroxide may be employed per one part by weight of taratannin.

Any suitable concentration of tannin may be employed in the reaction mixture. Advantageously, the concentration of tannin is from about 0.5 to about 10 lbs. of tannin per gallon of solvent, preferably from about 2 to about 8 lbs./gal., and more preferably from about 3 to about 6 lbs./gal.

All the methylation agent and the alkaline agent can be added initially and simultaneously or in any sequence. Alternatively, these agents can be added incrementally with heating and agitation of the reaction mixture.

In a preferred embodiment, the methylation agent and alkaline agent are added simultaneously and incrementally over a period of from about 4 to about 10 hours at a reaction temperature of from about 20° to about 60° C. (Optionally, the reaction mixture can be agitated for an additional period, e.g., from about 2 to about 6 hours, at a reaction temperature of about 20° to about 60° C., to aid in maximizing the extent of methylation).

With or without such additional agitation, hydrolysis of the resulting methylated tannin is thereafter effected by heating with agitation under hydrolysis conditions, e.g., maintenance of a reaction temperature of about 60° to about 110° C. for about 0.5 to about 6 hours. Heating with agitation can be effected advantageously by refluxing the reaction mixture. Preferred hydrolysis conditions include maintenance of a reaction temperature of about 80° to about 105° C. for about 1 hour to about 4 hours. (Optionally, at this stage, the reaction mixture is cooled and any precipitated side products are removed by filtration, centrifuging or the like.)

The above-described hydrolysis involves reaction of the methylated tannin with a hydrolysis agent under alkaline hydrolysis conditions to form a salt of TMB acid and the hydrolysis agent. Suitable hydrolysis agents include, for example, sodium hydroxide, potassium hydroxide, calcium hydroxide, ammonium hydroxide, organic amines (e.g., triethylamine), etc. The same material can serve as both the alkaline agent in the methylation step and as the hydrolysis agent in the hydrolysis step. Sodium hydroxide is preferred for use as both the alkaline agent and the hydrolysis agent. The amount of sodium hydroxide required for hydrolysis may be added to the reaction mixture prior to, during, or after the methylation reaction.

The above given amounts of sodium hydroxide generally will suffice to serve both the alkaline agent and hydrolysis agent functions. If desired an additional amount of sodium hydroxide or other hydrolysis agent may be added after methylation to aid in maximizing hydrolysis of the methylated tannin.

Advantageously, hydrolysis of the methylated tannin can be effected without isolation thereof from the reaction mixture.

Preferably, both the methylation step and the hydrolysis step are carried out under an inert atmosphere, preferably nitrogen, and in the presence of an oxygen scavenger, preferably sodium bisulfite.

After completion of the hydrolysis, TMB acid can be formed by neutralizing the 3,4,5-trimethoxybenzoate salt contained in the reaction mixture by acidifying with any suitable acid. Preferably, the reaction mixture is cooled, e.g., to about 15° to about 45° C., prior to neutralization. Suitable acids include, for example, hydrochloric acid, sulfuric acid, phosphoric acid, etc. The acid employed is admixed with the reaction mixture, preferably by slowly adding the acid to the reaction mixture. The acid is added in an amount sufficient to acidify the mixture to a pH in the acid range, desirably from about 1 pH to about 6 pH, and preferably from about 3 pH to about 5 pH. Hydrochloric acid is preferred as the neutralizing agent. The acid may be employed as an aqueous solution or in the form of a solution thereof in an organic solvent, e.g., methanol, chloroform, etc.

Practice of the present invention is illustrated by the following non-limiting examples. All parts and percentages given throughout this disclosure, including the claims which follow, are by weight unless otherwise indicated.

EXAMPLE 1

Preparation of 3,4,5-Trimethoxybenzoic Acid from Aqueous Taratannin

To 250 ml of aqueous taratannin (gallic acid content approximately 102 grams, 0.6 mole) are added 192 grams of 50% NaOH and 240 grams of Dimethyl sulfate in portions at 20°-40° C. over a 3-6 hour period. The reaction mixture is refluxed for 1-3 hours with 48 grams of 50% NaOH. Upon cooling to 30°-60° C., 48 grams of 50% NaOH and 120 grams of dimethyl sulfate are added in portions over a 2-4 hour period. After treating with an additional 48 grams of 50% NaOH, the reaction mixture is refluxed for 1-3 hours. At the end of hydrolysis, the reaction mixture is cooled and acidified with concentrated hydrochloric acid to precipitate 3,4,5-trimethoxybenzoic acid (TMB acid). The precipitated product is isolated and dried to give 107-112 grams of TMB in 84-87% yield.

EXAMPLE 2

Preparation of 3,4,5-Trimethoxybenzoic Acid from Aqueous Taratannin

To a 50 gallon reactor containing 108 lbs. of aqueous taratannin (gallic acid content approximately 34.6 lbs), charge 72 lb of 50% NaOH and 90 lbs of dimethyl sulfate in portions over a 2-6 hour period while maintaining a temperature of 20°-40° C. Then, the reaction mixture is refluxed for 2-4 hours with 21 lbs of 50% NaOH. Upon cooling to 30°-60° C., the reaction mixture is treated with 45 lbs of dimethyl sulfate and 18 lbs of 50% NaOH over a 2-4 hour period. Then, after the addition of an additional 27 lbs of caustic, the reaction solution is refluxed for 2-4 hours. Upon completion of hydrolysis, the reaction mixture is cooled, acidified to 3-5 pH with concentrated hydrochloric acid to yield 36-37 lbs. of dried 3,4,5-trimethoxybenzoic acid in 84-86% yield.

BEST MODE CONTEMPLATED

The best mode contemplated for carrying out this invention has been set forth in the above description, for example, by way of setting forth preferred materials and operating conditions, including but not limited to preferred ranges and values of amounts and other nonobvious variables material to successfully practicing the invention in the best way contemplated at the time of executing this patent application.

It is understood that the foregoing detailed description is given merely by way of illustration and that many modifications may be made therein without departing from the spirit or scope of the prsent invention.

What is claimed is:

1. A process for preparing a salt of 3,4,5-trimethoxybenzoic acid, which comprises:
   (a) reacting hydrolyzable tannin with a methylation agent in an alkaline medium under methylation conditions to form methylated tannin, and
   (b) hydrolyzing the methylated tannin by reaction thereof with a hydrolysis agent under alkaline hydrolysis conditions to form a 3,4,5-trimethoxybenzoate salt of the hydrolysis agent.

2. A process for preparing 3,4,5-trimethoxybenzoic acid (TMB acid) which comprises:
   (a) reacting hydrolyzable tannin with a methylation agent in an alkaline medium under methylation conditions to form methylated tannin, (b) hydrolyzing the methylated tannin by reaction thereof with a hydrolysis agent under alkaline hydrolysis conditions to form a 3,4,5-trimethoxybenzoic salt of the hydrolysis agent, and (c) neutralizing the trimethoxybenzoate salt to form 3,4,5-trimethoxybenzoic acid.

3. The process of claim 1 or 2 wherein said methylation agent is dimethyl sulfate, methyl p-toluene sulfonate, methyl iodide or diazomethane.

4. The process of claim 1 or 2 wherein said alkaline medium includes an alkaline agent selected from the group consisting of sodium, potassium, ammonium and calcium hydroxide and triethylamine.

5. The process of claim 1 or 2 wherein said hydrolysis agent is selected from the group consisting of sodium, potassium, ammonium, and calcium hydroxide and triethylamine.

6. The process of claim 1 or 2 wherein said hydrolysis is effected in situ without isolation of said methylated tannin.

7. The process of claim 1 or 2 wherein said tannin is taratannin.

8. The process of claim 1 or 2 wherein said methylation agent and said hydrolysis agent are employed in amounts of from about 2.5 to about 5 parts and from about 2.5 to about 4.5 parts, respectively, per 1 part of tannin.

9. The process of claim 1 or 2 wherein said methylation is carried out at a temperature of from about 20° to about 60° C. and said hydrolysis step is carried out at a temperature of from about 60° to about 110° C.

10. The process of claim 1 or 2 wherein the methylated tannin formed in step (a) is hydrolyzed in step (b) without separation of the methylated tannin into components.

11. A process for preparing a salt of 3,4,5-trimethoxybenzoic acid, which comprises:

(a) reacting hydrolyzable tannin obtained from a tannin-containing material selected from the group consisting of tara pods, Chinese nut galls, Aleppo galls and sumac leaves with a methylation agent in an alkaline medium under methylation conditions to form methylated tannin, and (b) hydrolyzing the methylated tannin by reaction thereof with a hydrolysis agent under alkaline hydrolysis conditions to form a 3,4,5-trimethoxybenzoate salt of the hydrolysis agent.

12. A process for preparing 3,4,5-trimethoxybenzoic acid (TMB acid) which comprises:

(a) reacting hydrolyzable tannin obtained from a tannin-containing material selected from the group consisting of tara pods, Chinese nut galls, Aleppo galls and sumac leaves with a methylation agent in an alkaline medium under methylation conditions to form methylated tannin, (b) hydrolyzing the methylated tannin by reaction thereof with a hydrolysis agent under alkaline hydrolysis conditions to form a 3,4,5-trimethoxybenzoate salt of the hydrolysis agent, and (c) neutralizing the trimethoxybenzoate salt to form 3,4,5-trimethoxybenzoic acid.

13. The process of claim 11 or 12 wherein the methylated tannin formed in step (a) is hydrolyzed in step (b) without separation of the methylated tannin into components.

14. The process of claim 11 or 12 wherein said methylation agent is dimethyl sulfate, methyl p-toluene sulfonate, methyl iodide or diazomethane.

15. The process of claim 11 or 12 wherein said alkaline medium includes an alkaline agent selected from the group consisting of sodium, potassium, ammonium and calcium hydroxide and triethylamine.

16. The process of claim 11 or 12 wherein said hydrolysis agent is selected from the group consisting of sodium, potassium, ammonium and calcium hydroxide and triethylamine.

17. The process of claim 11 or 12 wherein said hydrolysis is effected in situ without isolation of said methylated tannin.

18. The process of claim 11 or 12 wherein said tannin is taratannin.

19. The process of claim 11 or 12 wherein said methylation agent and said hydrolysis agent are employed in amounts of from about 2.5 to about 5 parts and from 2.5 to about 4.5 parts, respectively, per 1 part of tannin.

20. The process of claim 11 or 12 wherein said methylation is carried out at a temperature of from about 20° to about 60° C. and said hydrolysis step is carried out at a temperature of from about 60° to about 110° C.

* * * * *